(12) United States Patent
Young et al.

(10) Patent No.: US 6,448,040 B1
(45) Date of Patent: Sep. 10, 2002

(54) INHIBITOR OF CELLULAR PROLIFERATION

(75) Inventors: Craig Young, Munich; Friedrich Lottspeich, Stockdorf, both of (DE); Adam Otasek, Ottensheim (AT)

(73) Assignee: Max-Planck-Gesellschaft zur Förderung der Wissenschaften e.V., Berlin (DE)

(*) Notice: Subject to any disclaimer, the term of this patent is extended or adjusted under 35 U.S.C. 154(b) by 0 days.

(21) Appl. No.: 09/446,880

(22) PCT Filed: Jun. 29, 1998

(86) PCT No.: PCT/EP98/03973
§ 371 (c)(1),
(2), (4) Date: Mar. 15, 2000

(87) PCT Pub. No.: WO99/01551
PCT Pub. Date: Jan. 14, 1999

(30) Foreign Application Priority Data

Jun. 20, 1997 (EP) .............................. 97110669

(51) Int. Cl.[7] .................. C12N 15/00; C12N 15/63; C12N 15/85; C12Q 1/68; C07H 21/04
(52) U.S. Cl. ..................... 435/69.1; 435/4; 435/6; 435/320.1; 435/325; 435/455; 536/23.1; 536/23.5
(58) Field of Search .......................... 514/44; 424/93.1, 424/93.21; 435/69.1, 320.1, 325, 455, 4, 6; 536/23.1, 23.5

(56) References Cited

FOREIGN PATENT DOCUMENTS

WO   WO 96254921   *  8/1996   ............ C12N/15/12

OTHER PUBLICATIONS

Das et al. Mol Cell Bio Jun. 2000;20:3942–50.*
Eck et al. The Pharmarcological Basis of Therapeutics. 1995; pp77–101.*
Schnier et al. Mol Cell Bio Jun. 1991;11:3105–14.*

* cited by examiner

Primary Examiner—James Ketter
Assistant Examiner—Q. Janice Li
(74) Attorney, Agent, or Firm—Albert P. Halluin; Viola T. Kung; Howrey, Simon, Arnold & White, LLP

(57) ABSTRACT

The present invention relates to nucleic acid molecules encoding hypusines mutants having the biological activity of an inhibitor of cellular proliferation. The present invention further relates to vectors comprising said nucleic acid molecules, to hosts transformed with said vectors, to methods of producing the polypeptide encoded by the nucleic acid molecule of the invention as well as to the polypeptide itself. In addition, the present invention relates to pharmaceutical and diagnostic compositions comprising one or more of the aforementioned compounds, the methods for synchronizing cell growth and to the use of the vector of the invention in gene therapy.

25 Claims, 5 Drawing Sheets

Figure 5

Human cDNA 1-465
atggcagatgacttggacttcgagacaggagatgcaggggcctcagccaccttcccaatgcagtgctcagcattacgtaag
aatggctttgtggtgctcaaaggccggccatgtaagatcgtcgagatgtctacttcgaagactggcaagCACggccacg
ccaaggtccatctggttggtattgacatctttactgggaagaaatatgaagatatctgcccgtcaactcataatatggatgtccc
caacatcaaaaggaatgacttccagctgattggcatccaggatgggtacctatcactgctccaggacagcggggaggtacg
agaggaccttcgtctccctgagggagaccttggcaaggagattgagcagaagtacgactgtggagaagagatcctgatca
cggtgctgtctgccatgacagaggaggcagctgttgcaatcaaggccatggcaaaataa
155 amino acids
MADDLDFETGDAGASATFPMQCSALRKNGFVVLKGRPCKIVEMSTSKTGKH
GHAKVHLVGIDIFTGKKYEDIC-
PSTHNMDVPNIKRNDFQLIGIQDGYLSLLQDSGEVREDLRLPEGDLGKEIEQKY
DCGEEILITVLSAMTEEAAVAIKAMAK

Figure 6

Yeast 474bp
atgtctgacgaagaacataccttttgaaactgctgacgctggttcctccgccacctacccaatgcaatgttctgccttgagaaag
aacggtttcgttgtcatcaagagtagaccatgtaagattgtcgacatgtccacttctaagactggtAAGcacggtcacgcta
aagtccatttggttgccattgatatcttcactggtaagaagttggaagatttgtctccatctactcacaacatggaagttccagttg
tcaagagaaacgaataccaattgttggacattgatgacggtttcttgtctttgatgaacatggacggtgacactaaggatgatgt
caaggctccagaaggtgaattgggtgacagtttgcaaactgcttttgatgaaggtaaggacttgatggttaccatcatctccgc
tatgggtgaagaagccgccatctccttcaaggaagctgctagaaccgattaa
157 amino acids
MSDEEHTFETADAGSSATYPMQCSALRKNGFVVIKSRPCKIVDMSTSKTGKH
GHAKVHLVAIDIFTGKKLEDLSPSTHNMEVPVVKRNEYQLLDIDDGFLSLMN
MDGDTKDDVKAPEGELGDSLQTAFDEGKDLMVTIISAMGEEAAISFKEAART
D

Figure 7

Dictyostelium 510bp
atgaaaccattaataatggagtacaacaaaatgtcagataacgaagctttagatgtcgaagactacgcccaagccggttcag
gtgcttcattaaccttcccaattcaatgttcagcattaagaaagaacggtttcgtcgtcattaaaggtttcccatgtaagattgttg
atatgtcaacttccaaaaccggtAAAcacggtcacgccaaagttaacatcactgctatcgatatcttcactggtaagaaata
cgaagaaatttgcccatcaactcacaacattgatgtaccaaatgtcagcagaaaggaatacaccgttatggatgttcaagatg
gttacttatcactcttggatgctggtggtgaagtcaaagaagatcttgccctcccagaagatgatattggtaaagaaattaccca
aatgttaaaagaaggtaaagagccattagtttcagtcatctctgctttaggtaaagaaggtgtcgtctctgttaaagtcagcaac
aattaa
169 amino acids
MKPLIMEYNKMSDNEALDVEDYAQAGSGASLTFPIQCSALRKNGFVVIKGFP
CKIVDMSTSKTGKHGHAKVNITAIDIFTGKKYEEICPSTHNIDVPNVSRKEYTV
MDVQDGYLSLLDAGGEVKEDLALPEDDIGKEITQMLKEGKEPLVSVISALGKE
GVVSVKVSNN

INHIBITOR OF CELLULAR PROLIFERATION

CROSS REFERENCES TO OTHER APPLICATIONS

The Application is a National Stage of International Application PCT/EP98/03973, filed Jun. 29, 1998; which claims the priority of EP 9711 0669.5, filed Jun. 20, 1997.

FIELD OF THE INVENTION

The present invention relates to nucleic acid molecules encoding hypusine mutants having the biological activity, of inhibiting cellular proliferation.

SUMMARY OF THE INVENTION

The present invention further relates to vectors comprising said nucleic acid molecules, to hosts transformed with said vectors, to methods of producing the polypeptide encoded by the nucleic acid molecule of the invention as well as to, the polypeptide itself. In addition, the present invention relates to pharmaceutical and diagnostic compositions comprising one or more of the aforementioned compounds, to methods for synchronizing an/or retarding cell growth and to the use of the vector of the invention in gene therapy.

BACKGROUND OF THE INVENTION

The study of cell cycle has been one of the long standing interests of microbiologists and molecular biologists. Early work in molecular biology, for example, identified the myc-protein as one of the key regulators of cell division. Since this regulation of cell division might well have a crucial impact on processes generally known as neoplastic transformation, studies on cell cycle regulation naturally also have enjoyed a special interest in the medical field.

In order to more fully understanding cellular division, it is important to have a means at hand that interferes with, stops or synchronizes the cell cycle. In the past, a number of components that fulfill these requirements have been identified. Thus, temperature sensitive mutants such as cyclins, cdc 25 which at restrictive result in G2 arrest, chemotherapeutic agents like methotrexate or fluorouracil act as powerful inhibitors of DNA replication.

However, many of these compounds have an irreversible effect on the cell cycle. These as well as other compounds having similar properties are eventually toxic for the cells and accordingly of limited value, in particular with regard to pharmaceutical applicability.

The technical problem underlying the present invention was therefore to provide a means that can be conveniently employed in the study of cell cycle without having the adverse effects of the compounds known in the art. The solution to said technical problem is achieved by providing the embodiments characterized in the claims.

Accordingly, the present invention relates to a nucleic acid molecule encoding a polypeptide having the biological activity of inhibiting cellular proliferation selected from the group consisting of:

(a) nucleic acid molecules hybridizing to a complementary strand of a nucleic acid molecule comprising the nucleotide sequence shown in FIG. 5 (SEQ ID NO:1) or 6 (SEQ ID NO:3) and/or of a nucleic acid molecule coding for a polypeptide comprising the amino acid sequence shown in FIG. 5 (SEQ ID NO:2) or 6 (SEQ ID NO:4); and (b) nucleic acid molecules, the nucleotide sequence of which is degenerate as a result of the genetic code to a nucleotide sequence of a nucleic acid molecule as defined in (a).

Figure 1:
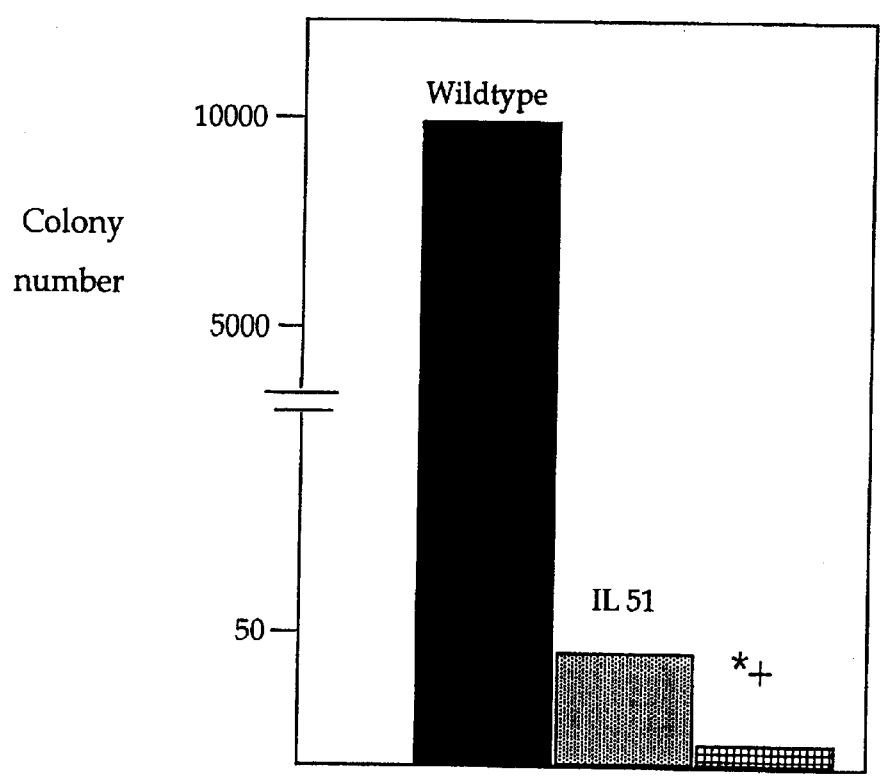
FIG. 1: The number of surviving colonies after FOA screening Wildtype, where position 51 is lysine which is modified to hypusine. IL51, where position 51 is mutated to the codon for isoleucine. +, negative control, pRS 413 alone*, where all other remaining codons are for alanine, arginine, asparagine, aspamc acid, cysteine, glutamine, glutamic acid, glycine, histidine, leucine, methionine, phenylalanine, proline, serine, threonine, tryptophan, tyrosine or valine.

The 19 PCR fragments together with wildtype as a positive control were cloned into the low copy number plasmid pRS413 (Sandholzer, U. Centea, lntemann M., Noegel, A. A., Lottspeich, F. FEBS (Federation of European Biochemical Societies) Letters, 246, 94–99 (1989), containing both Hyp2 and Hyp1 disruptions complemented by the multicopy plasmid YEp 352 harboring the auxotrophic marker for uracil (URA 3) and the gene encoding the hypusine containing protein from Dictyostelium discoideum again downstream of the GAL1 promoter fragment. The cells were grown to mid log phase in 2 ml of galactose containing minimal medium, spun down and resuspended in a residual volume which was then plated out on FOA containing histidine, tryptophan, leucine deficient plates using 2% galactose, 1.5% raffinose as a carbon source. The plates were incubated at 30° C. for a period of 5 days after which time the plates were scored for colony growth, FIG. 1 shows the mean result of three such independent screens. We investigated these colonies to see if indeed the selective shuffle had worked by scoring growth on uracil deficient medium. No growth was observed from colonies obtained after both the wildtype and isoleucine 51 FOA screening. Thus, it was assumed that the URA 3 harboring Yep plasmid was no longer present.

Figure 2:
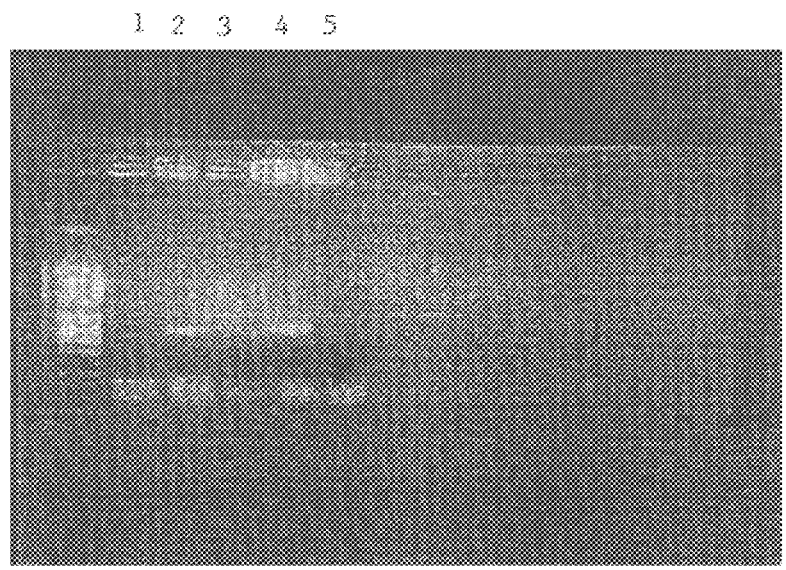
Figure 3:
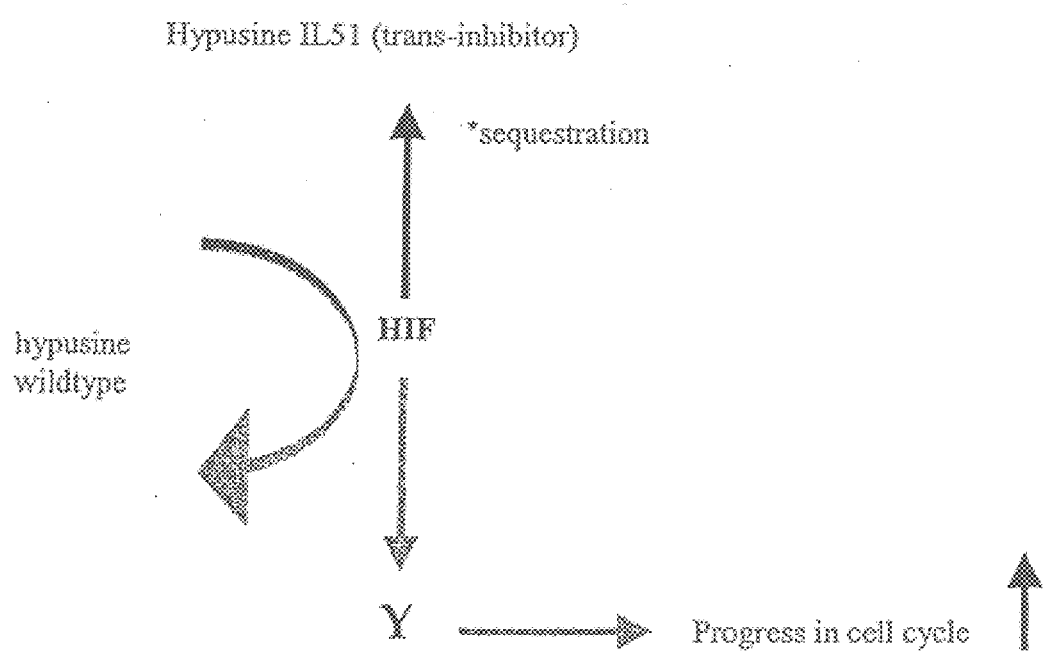

FIG. 2: Direct PCR analysis of FOA screened clones PCR from colonies after FOA screening Lane 1: negative control Lane 2: Dictyostelium Lane 3: Dictyost&rm PCR set after wildtype screening Lane 4: Human PCR after IL51 screening Lane 5: Negative control FIG. 3: Model of action of hypusine mutant transinhibition of functional wildtype homolog.

Figure 4A:
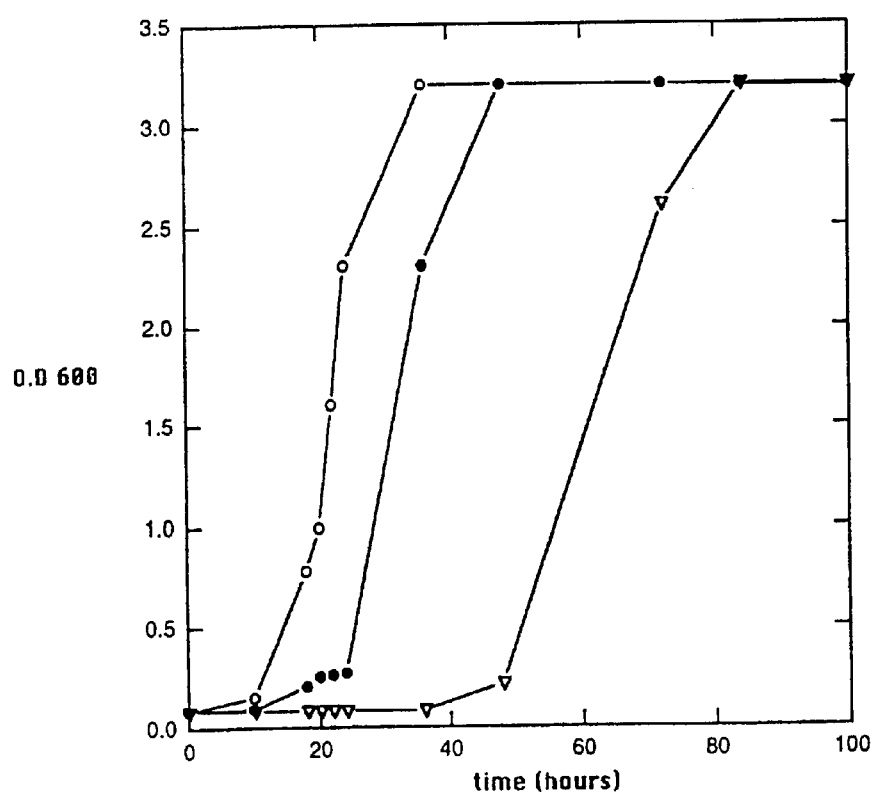
Figure 4B:
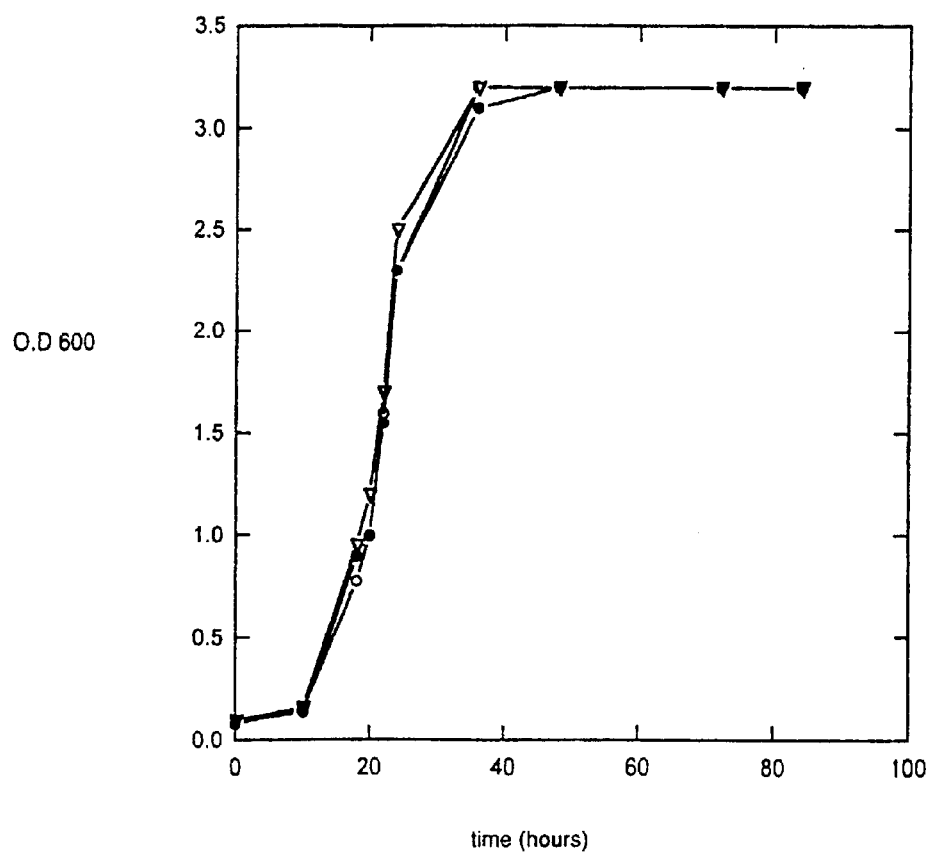

FIG. 4a–4b: Overexpression of hypusine mutant -IL51 on galactose-containing medium. 4a WT grown on galactose as a carbon source YEp 3521L51 grown on galactose as a carbon source pHR81IL51 grown on galactose as a carbon source, leucine deficient medium 4b WT grown on galactose as a carbon source YEp 3521L51 grown on glucose as a carbon source pHR81 IL51 grown on glucose as a carbon source FIG. 5: cDNA (SEQ ID NO:1) and amino acid sequence (SEQ ID NO:2) of the human hypusine gene. The position of amino acid His 51 is indicated in capital and underlined.

FIG. 6: cDNA (SEQ ID NO:3) and amino acid sequence (SEQ ID NO:4) of the yeast hypusine gene.

The position of amino acid Lys 51 (hypusine modification) is indicated in capital and underlined.

FIG. 7: cDNA (SEQ ID NO:5) and amino acid sequence (SEQ ID NO:6) of the dictyostelium hypusine gene.

The position of amino acid Lys 65 (hypusine modification) is indicated in capital and underlined.

DETAILED DESCRIPTION OF THE PREFERRED EMBODIMENTS

It is well known in the art that hypusine, otherwise known as eIF5A, a protein that is widespread among eukaryots and archaebacteria, is highly conserved (Park et al., Trends in Biochemical Sciences 18 (1993)475–479). Characteristically in the yeast eIF5A homologue, lysine51 is post-translationally modified to the amino acid hypusine by the transfer of an aminobutyl moiety from spermidine and its subsequent hydroxylation in a two step enzymatic reaction. The function of eIF5A is as yet not determined. Initially supposed to be involved in the translation initiation (Cooper et al., Proc. Natl. Acad. Sci. USA 80 (1985), 1854–1857), it is now thought that the hypusine containing protein may play a vital role in the control of cellular proliferation (Kang and Hersey, J. Biol. Chem. 269 (1995), 3934–3940; Schnier et al., Mol. Cell. Biol. 11 (1991), 3105–3114), the exact mechanistic details are, however, unknown.

Since the amino acid hypusine is rather uncommon in nature, it has been speculated that its presence is absolutely necessary for the function of the hypusine protein. Exchange of the amino acid hypusine by any other of the 20 naturally occurring amino acids resulted in the loss of the natural biological function of the hypusine protein as was shown in accordance with the present invention. However, the substitution of a number of amino acids such as lysine at position 51 for isoleucine in the yeast molecule or histidine at position 51 for lysine in the human molecule yielded a protein with novel and surprising properties. Namely, it could be shown that by overexpressing a site-specific mutated form of the yeast Hyp2 protein, wherein isoleucine replaces hypusine at position 51, the cell cycle is arrested. This arrest is both non-toxic and reversible. It was even more surprising that a similar finding was connected to the exchange of the amino acid lysine at position 51 human hypusine protein which corresponds to position 52 of the yeast protein by histidine. It is expected that corresponding exchanges in the respective other protein, namely Lys to Ile in pos. 50 of the human molecule and His to Lys in position 52 of the yeast molecule will give identical or similar results. These findings of the present invention have enormous implications in the areas of microbiology, molecular biology and medicine. The specific applications will be discussed in more detail herein below and include the study of apoptosis as well as of cell cycle regulation. It is expected that other mutations in the hypusine protein have the same effect that is described in accordance with the present invention. Such mutations comprise substitutions, deletions and insertions, in particular in the hypusine consensus region of positions 30 to 80 of the yeast hypusine protein, as well as in regions of the hypusine protein of other organisms corresponding to said region.

As was stated above, the hypusine protein is common to both the eukaryotic and archaebacterial kingdoms. Although this protein is highly conserved, the exact position of the amino acid hypusine and the protein hypusine does vary to some extent, also depending on the overall length of the polypeptide chain. For example, the amino acid hypusine occurs in the corresponding Dictyostelium protein at position 65. The analysis of nucleotide or amino acid sequences from respective proteins from other organisms may identify the lysine that is posttranslationally converted to hypusine in still other positions of the polypeptide chains.

Yet, all nucleic acid molecules encoding the highly conserved hypusine proteins from said various sources and the complementary strands thereof are expected to cross-hybridize under appropriately selected hybridization conditions. Said hybridization conditions are preferably stringent hybridization conditions. For a definition of the term "stringent hybridization conditions" see, for example, Sambrook et al., "Molecular Cloning: A Laboratory Manual", second edition 1989, CSH Press, Cold Spring Harbor, or "Nucleic Acid Hybridization, A Practical Approach", Editors Hames & Higgins, IRL Press, Oxford 1985. Further, all hypusine proteins obtainable from the above-referenced sources have been shown or are expected to comprise the amino acid hypusine since this rare amino acid, is expected to be essential for function. The replacement of the amino acid lysine that is post-translationally modified to yield hypusine, by isoleucine is, due to the strong conservation of this system, in all or nearly all hypusine proteins from different origins expected to result in the same advantageous properties that have been observed with the yeast protein. The same holds true for other mutations, in particular in the hypusine conserved regions, such as mutations in hypusines from other organisms like Dictyostelium corresponding to the human HypusinLYS51 mutation. Accordingly, all nucleic acid molecules that deviate from the nucleotide sequence depicted in FIG. 5 (SEQ ID NO:1) or 6 (SEQ ID NO:3) by insertion, deletion, point mutation or otherwise but hybridize thereto, wherein the protein encoded thereby retains the capability of inhibiting cellular proliferation and, for example, comprises an isoleucine instead of a hypusine, are included in the present invention. Similarly, the present invention covers nucleic acid molecules that deviate from the above-references nucleic acid molecules by the degeneracy of the genetic code.

The nucleic acid molecules of the invention may be DNA such as cDNA or RNA such as mRNA. Its origin:may be natural, synthetic or semisynthetic. Said nucleic acid molecules may encode merely the hypusine mutants of the invention or fusion proteins comprising said mutants. The nucleic acid molecules of the invention may also be fragments of the nucleic acid molecules identified in the accompanying figures that retain the biological activity of the inhibitor.

In a preferred embodiment of the invention, said nucleic acid encodes a polypeptide wherein said polypeptide comprises the region corresponding to amino acid positions 30 to 80 of the amino acid sequence shown in FIG. 6 (SEQ ID NO:4) and/or the corresponding region in FIG. 5 (SEQ ID NO:2) but differs therefrom by at least one mutation selected from the group of amino acid substitutions and nucleic acid or amino acid deletions or insertions. Said region corresponds to the hypusine conserved region (Park et al., J. Biol. Chem. 269 (41)(1994)12916–12921). It is particularly preferred that said mutation is an amino acid substitution clustering around amino acid position 51 or 52 of yeast hypusine or at a corresponding position of a hypusine molecule from a different organism, such as positions 50 and 51 of human hypusine.

In a further preferred embodiment, the nucleic acid molecule of the present invention comprises the nucleotide sequence shown in FIG. 5 (SEQ ID NO:1) or 6 (SEQ ID NO:3) or which encodes a polypeptide comprising the amino acid sequence shown in FIG. 5 (SEQ ID NO:2) or 6 (SEQ ID NO:4), wherein the lysine residue corresponding to position 51 of the amino acid sequence shown in FIG. 6 (SEQ ID NO:4) is replaced by the amino acid isoleucine and/or the histidine residue in position 51 of the amino acid sequence shown in FIG. 5 (SEQ ID NO:2) is replaced by the amino acid lysine. This embodiment of the invention is particularly advantageously employed, if it is intended to apply the yeast or human hypusine system for inhibiting, retarding or reversing the inhibiting of the cell cycle. Also comprised by the invention are sequences that hybridize to the aformentioned sequences, preferably under stringent conditions, as well as sequences that are degenerate with regard to the hybridizing sequences. All these sequences encode proteins that have the above mentioned inhibiting effect.

Stringent hybridization conditions are well known in the art (see, e. g., Sambrook et al., "Molecular Cloning: A Laboratory Manual", second edition 1989, CSH Press, Cold Spring Harbor, or "Nucleic Acid Hybridization, A Practical Approach", Editors Hames & Higgins, IRL Press, Oxford 1985) and refer, e.g., to hybridization in a buffer comprising 6×SSC, 0.1% SDS at 65–68° C. and washing in 0. 1–0.2× SSC, 0.1% SDS at 65–68° C. Alternative stringent conditions are, e.g., hybridization in a buffer comprising 50% formamide, 5×SSPE, 0.1% SDS at 42° C. and washing as above.

In a further preferred embodiment of the present invention, said nucleic acid sequence is derived from an archaebacterium, a fungus, a plant, an animal or a human.

For pharmaceutical applications, it is most preferred that said nucleic acid sequence is derived from a human. Further particularly preferred is that said fungus is Saccharyomyces cerevisiae.

Another preferred embodiment of the invention relates to a nucleic acid sequence that encodes the polypeptide yeast hypusinIL51 or the polypeptide human hypusinLYS51. Both polypeptides owing to their trans-dominant effect on cellular proliferation are particularly suited to gene therapeutic application owing to the fact that the aforementioned inhibition is, by definition, dosage dependent. This ensures that any leaky expression in neighboring healthy tissues is negligible and therefore beneficial to the well-being of the patient.

In addition, the present invention relates to a vector comprising the nucleic acid molecule of the invention. Said vector may be a vector useful for propagating the genetic material contained therein.

Preferably, said vector is an expression vector or a targeting vector. It is most preferably selected from the group consisting of a retroviral vector, an adenoviral vector, an EBV-based vector and a hepatitis B virus-based vector.

In an additional most preferred embodiment, the vector of the invention comprises a regulatory element which is derived from a strong promoter. Said strong promoter is advantageously the galactose (galI)promoter. This embodiment is in most useful in systems where overexpression can be obtained by making galactose available to the cell.

In a further most preferred embodiment, said vector is the low-copy-plasmid pRSIL51 or the multi-copy-plasmid YEpIL51, the construction of which is shown in Example 1 or said vector is the low-copy-plasmid pRSLYS51 or the multi-copy-plasmid YEpLYS51, the construction of which is shown in Example 2.

The present invention also relates to hosts comprising the nucleic acid molecule of the invention or the vector of the invention. The nucleic acid molecule of the vector of the invention may be introduced by any method available into said host. Conventional methods are, for example, transfection or transformation, particle bombardment, electroporation, micro-injection or liposome fusion. The nucleic acid molecule would, as a rule, be expected to be incorporated into the chromosome(s) of the host whereas the vector may be retained in chromosomally integrated or extrachromosomal form.

Preferably, the host of the invention is a eukaryotic, eubacterial or archaebacterial host. Most preferably, it is a transgenic plant or mammal, a mammalian cell, an insect cell, a yeast cell, preferably a Saccharomyces cerevisiae cell or a fungus, preferably a Dictyostelium discoideum cell. Transgenic mammals excluding humans would, of course, be preferred in testing pharmaceutical applications which will be explained in more detail herein below. In contrast, Saccharomyces cerevisiae or Dictyostelium discoideum may advantageously be used for producing the protein or for carrying out investigations with regard to the molecular mechanism underlying the hypusine function. Transgenic mammals or insect cells can also be used for producing the protein.

The present invention also relates to a method for the production of the polypeptide encoded by the nucleic acid molecule of the invention comprising raising/culturing a host of the invention under conditions allowing the expression of the polypeptide and recovering the polypeptide.

A large number of suitable methods exist in the art to produce proteins in appropriate hosts. If the host is a unicellular organism or a mammalian or insect cell, the person skilled in the art can revert to a variety of culture conditions that can be further optimized without an undue burden of work. Conveniently, the produced protein is harvested from the culture medium. If the protein is not exported into the medium, it can alternatively be extracted from the host cells by established techniques. If the host is a transgenic mammal, the protein may, for example, be found in the milk and recovered therefrom.

Additionally, the present invention relates to a polypeptide that is encoded by the nucleic acid molecule of the invention or produced by the method of production of the invention. The polypeptide of the invention may accordingly be produced by microbiological methods or by transgenic mammals. It is also envisaged that the polypeptide of the invention is recovered from transgenic plants. Alternatively, the polypeptide of the invention may be produced synthetically or semi-synthetically.

The present invention further relates to a pharmaceutical composition comprising the vector of the invention and/or the polypeptide of the invention and a pharmaceutically acceptable carrier.

As is immediately evident to the person skilled in the art, the advantageous properties of the polypeptide of the invention has, a wide applicability in the medical field. It is envisaged that the presence or overexpression of the nucleic acid sequence of the protein of the invention has a beneficial effect in the treatment of all diseases that are based on hyperproliferative cell division. Examples of said diseases are all forms of cancerous conditions. Accordingly, the present invention can be applied in tumor therapy. In this type of therapy as well as in other types of diseases, the person skilled in the art would decide whether the pharmaceutical composition should comprise the vector or protein of the invention or both. As regards the tumor therapy, it is envisaged that using a gene therapeutic approach, the vector of the invention is introduced into the tumor cells and the nucleic acid molecule of the invention is subsequently expressed whereupon the tumorous growth of these cells would be stalled. The pharmaceutical composition of the invention is expected to be successfully and beneficially applicable in the treatment of all solid tumor forms and all leukemia forms.

A further type of disease that may be successfully treated by the application of the pharmaceutical composition of the invention is a hyperproliferative skin disease such a psoriasis. In this case, a topical application of the composition might be most advantageous. The pharmaceutical composition of the invention may also be useful in the treatment of restenosis, psoriasis, melanomas or other cancerous conditions.

The dosage regimen of the pharmaceutical composition to be applied will be determined by the attending physician considering the condition of the patient, the severity of the disease and other clinical factors. Generally, the regimen as a regular administration of the pharmaceutical composition should be in the range of 1 g to 10 mg units per day. If the regimen is a continuous infusion, it should also be in the range of 1 g to 10 mg units per kilogram of body weight per minute, respectively. Progress can be monitored by periodic assessment. Administration of the suitable compositions may be effected by different ways, e.g. by intravenous, intraperitoneal, subcutaneous, intramuscular or topical route.

The pharmaceutical composition of the present invention can further be administered according to the above regimens in all disease states that would benefit from the regulated apoptosis of specific cells or tissue. Again, the vector and/or polypeptide of the invention would be introduced by appropriate means into said cells or tissue eventually leading to the desired death of said cells or tissue.

Of particular advantage for the applicability of the pharmaceutical composition of the invention is the fact that the polypeptide of the invention has proven to be non-toxic.

The present invention also relates to a diagnostic kit comprising (a) the nucleic acid molecule of the invention;

(b) the vector of the invention; and/or (c) the polypeptide of the invention.

The kit of the invention may be advantageously used for studying cellular mechanisms of cell growth as well as apoptosis in cells.

Furthermore, the present invention relates to a method for synchronizing and/or retarding cell growth comprising:

(a) overexpressing the nucleic acid molecule of the invention or the vector of the invention in a cell; and (b) after inhibition of cell growth, down-regulating said overexpression.

The method of the invention can advantageously be used for analyzing mechanisms that regulate the cell cycle.

Also, the present invention relates to the use of the vector of the invention for the preparation of a composition for gene therapy.

Finally, it could be shown in accordance with the present invention that fluoro orotic acid (FOA) can be employed for screening for dominant negative mutants. Therefore, the present invention also relates to the use of a fluoro-erotic acid screen for the selection of dominant negative mutants.

EXAMPLES

Example 1

Test for Requirement of the Amino Acid Hypusine for Function of the Hypusine Protein Using the yeast Saccharomyces cerevisiae as a model system, we set about testing whether the hypusine residue is absolutely essential for function. Lysine 51, the residue required for hypusine formation, was substituted using PCR megapriming for every naturally occurring amino acid. The site specific mutants were cloned into the low copy number vector pRS413 (Sikorski and Hieter, Genetics 122 (1989), 19–27). The constructs were transformed into a strain created to contain disruptions of both the Hyp1 and the Hyp2 loci, complemented by YEp 352 DIC (Sandelholzer et al., FEBS Lett. 246 (1989), 94–99) containing the functional homologous of eIF5a from *Dictyostelium discoideum*. The mutant containing strain was then used to perform a selective plasmid shuffle, using Fluro-orotic acid (FOA) (Boeke J D, Truehard J, Natsoulis G, Fink G R, Methods in Enzymology 8 (1987) 164–1 75) to counterselect the URA 3 harboring YEp plasmid. Plating cells of FOA containing medium allows the gene product of the URA 3 marker, orotidine-5'-phosphate decarboxylase, to convert FOA to the toxic product F-dUMP and in doing so negatively selecting against the presence of YEp 352 DIC. As hypusine is essential where the mutant allele cloned in pRS 413 is incapable of complementing wildtype, cells fail to survive on this medium long enough to form colonies. This method enabled the functional homologue from *D. discoideum* to be exchanged for a given mutated allele and was used to screen all 19 point mutations at position 51 in the yeast gene HYP2 for their ability to complement the disrupted strain. The results of the FOA screen can be seen in FIG. 1. As expected from what we know about the conservation of hypusine (Park et al., lot. cit.) no other amino acid complements at position 51. However, an exchange of the wildtype lysine to isoleucine reproducibly gave rise after 5 days to 40 colonies, whereas wildtype gave rise after two days 10,000. The extreme difference between colony number and time of appearance led us to believe that the isoleucine screening was influenced by additional events. In order to rule out the possibility that the 40 colonies were uracil transport mutants which were in some way defective in the ability to take up FOA or in their ability to metabolize uracil, we transformed several clones with the yeast integrating plasmid pRS406 (Sikorski R., Hieter P., Genetics 122 (1989) 19–27), containing the URA 3 genetic marker. Transformants were selected for on uracil deficient plates and the resulting integrants were grown to mid log phase and plated out on FOA plates as described in FIG. 1. No growth was observed, indicating that FOA was still being taken up and converted intracellularly to its toxic product 5-dUMP. Thus, trivial explanations for the consistent presence of a background of 40 colonies after isoleucine screening were eliminated.

This lead us to believe that the URA 3 gene had mutated at some point during the FOA screen and that the 40 remaining colonies had retained YEp 352 and therefore a functional copy of the *D. discoideum* homologue. On mutating, the copy number of the YEp plasmid becomes, for the first time, on exposure to FOA, FOA independent. This results in the rise of the number of copies of the YEp plasmid per cell, back to its starting level, estimated to be 10–20 times that of the pRS413 plasmid, having the effect that in plasmid rescue the YEp plasmid will be rescued with at least 10 times the probability of rescuing pRS413 accounting for the difficulty in rescuing this plasmid. Direct PCR analysis of FOA screened clones does in fact show the presence of both plasmids after screening with pRS IL5 1. The results are shown in FIG. 2.

Two hypotheses were postulated to explain this phenomenon, both of which assume that the IL5 1 mutant in some way prolongs the life span of cells exposed to FOA, thus allowing the mutation in the URA 3 gene to occur an effect not seen in any other screened point mutation at position 51. Firstly, it is possible that isoleucine 51 acts as a very poor complementer enabling the cells to survive on FOA long enough for the mutation to occur.

Secondly, an alternative hypothesis predicts that the IL5 1 mutant acts as a transinhibitor of the wildtype or functional homologue, i.e. Dictyostelium protein. In so doing the mutant would competitively inhibit the Dictyostelium protein, where its levels fall due to plasmid loss during the course of an FOA screen. At such time, according to the model, IL51 inhibits the ability of the wildtype or a functional homologue to convert a putative hypusine interacting factor to Y, whose accumulation allows the cells to progress in the cell cycle. The model is shown in schematic form in FIG. 3.

The upshot of such a model would be cell cycle arrest at a certain point during the FOA screen. If this arrest were to occur outside of the S phase compartment, FOA would no longer be able to act as an obligate chain terminator and thus be toxic to the cells.

To distinguish between one of the two alternative models proposed, the IL51 gene was cloned downstream of the Gal1 promoter in the multicopy YEp 352 plasmid. In this manner IL51 could be inducibly overexpressed. This construct was transformed into a diploid wildtype strain and grown to saturation in minimal medium containing glucose as a carbon source. The cells were then diluted 20-fold in both galactose containing medium and, serving as an control, glucose containing medium. The wildtype strain containing YEp DIC served as an additional control. The result of three such independent experiments can be seen graphically in FIGS. 4(a, b).

Where expression of IL51 from a multicopy plasmid is induced via addition of galactose, a growth inhibition is clearly detectable for 24 hours, during which time all other cultures are approaching saturation, showing this not to be a metabolic effect of galactose but rather an effect specifically mediated by the point mutant IL51. Thus, in short IL51 acts as a dominant negative effector of wildtype function. The effect is seen to be reversible as changing the medium of an arrested culture from galactose to glucose lifts the inhibition by reducing expression from the Gal1 promoter, allowing the cells to grow as wildtype control. The apparent relax of the inhibition after 18 hours may be due to loss of YEp352 as the expression of IL51 from the ultra high copy number plasmid pHR81 extends the inhibition to well over 60 hours. The inhibition is by no means restricted to overexpression of the yeast protein, as a site specific mutated form of the Dictyostelium protein, where the corresponding lysine, K65, is mutated to isoleucine shows a similar inhibition. This is indicative that the conserved regions of the protein are responsible for the observed inhibition. This finding supports the assumption that this mutant will have a similar activity in many cell types.

Example 2

Effect of Human HypusinLYS51 on the Cell Cycle

The neighboring residue to hypusine of the human protein, histidine 51 (corresponding to position 52 of the yeast protein), was mutated to lysine and cloned into pRS 413 yielding pRSLYS51. As before an FOA screen was performed. The result of the FOA screen was similar to the IL51 screening. However, even more colonies were obtained and on that basis the mutant was subcloned into the high copy number vector YEp352 yielding YEpLYS51. In overexpression studies the mutant performed as wild type when grown on glucose containing medium. However, on galactose containing medium one out of 20 clones tested showed strong inhibition. This result is consistent with the model for IL51 inhibition and although not every clone shows this phenotype is strongly suggestive of the fact that there may be several mutations within the hypusine consensus broadly defined by Park et al., loc. cit. to be Phe 30 to Asp 80 (J. Biol. Chem. 269 (41) 25916–21 1994). Mutations within this consensus should be expected to abrogate modification of the elF5a precursor and therefore may act in a similar inhibitory fashion as the discussed IL51 in the yeast and LYS51 in the human hypusine.

What is claimed is:

1. An isolated nucleic acid molecule encoding a polypeptide having the biological activity of inhibiting cellular proliferation, comprising the mutated nucleotide sequence (SEQ ID NO: 1) or (SEQ ID NO: 3), or a nucleic acid molecule coding for a polypeptide comprising the mutated amino acid sequence (SEQ ID NO: 2) or (SEQ ID NO: 4), wherein said polypeptide comprises the region corresponding to amino acid sequences residues 30 to 80 of the amino acid (SEQ ID NO: 4) or (SEQ ID NO: 2), wherein the mutated amino acid sequence has at least one mutation in said amino acid residues 30 to 80, and the mutated nucleic acid sequence has at least one mutation corresponding to said mutation in said amino acid residues 30 to 80.

2. The nucleic acid molecule according to claim 1, wherein
   (a) the lysine residue corresponding to position 51 of the amino acid sequence (SEQ ID NO: 4) is replaced by the amino acid isoleucine; and/or
   (b) the histidine residue in position 51 of the amino acid (SEQ ID NO: 2) is replaced by the amino acid lysine.

3. The nucleic acid molecule consisting of claim 1 derived from the group of an archaebacterium, a fungus, a plant, an animal and a human.

4. The nucleic acid molecule of claim 3, wherein the fungus is *Saccharomyces cerevisiae*.

5. The nucleic acid molecule of claim 1 or 2, wherein the polypeptide is yeast HypusinIL51 or human HypusinLYS 51.

6. A vector comprising the nucleic acid molecule of claim 1 or a nucleic acid molecule having the sequence of (SEQ ID NO: 1) or (SEQ ID NO: 3).

7. The vector of claim 6 which is an expression vector or a targeting vector.

8. The vector of claim 6 which is selected from the group consisting of a retroviral vector, an adenoviral vector, an EBV-based vector and a hepatitis B virus-based vector.

9. The vector of claim 6, comprising a regulatory element which is derived from a strong promoter.

10. The vector of claim 9, wherein the strong promoter is the galactose promoter (gal1).

11. The vector of claim 8 which is the low-copy-plasmid pRSIL51 or the multi-copy-plasmid YEpIL51, or which is the low-copy-plasmid pRSLYS51 or the multi-copy-plasmid YEpLYS51.

12. A host cell comprising the nucleic acid molecule of the vector of claim 6.

13. The host of claim 12 which is a eukaryotic, a eubacterial or an archaebacterial host.

14. The host cell of claim 13 which is a plant cell, a mammalian cell, an insect cell, a yeast cell, or a fungus.

15. The host cell of claim 14, wherein the yeast cell is a *Saccharomyces cerevisiae* cell, wherein the fungus is *Dictyostelium discoideum* cell.

16. A method for the production of a polypeptide encoded by the nucleic acid of claim 1 or the nucleic acid molecule (SEQ ID NO: 1) or (SEQ ID NO: 3) comprising culturing a host cell of claim 12 under condition.

17. An isolated polypeptide encoded by the nucleic acid of claim 1.

18. A composition comprising the polypeptide of claim 17 and a pharmaceutically acceptable carrier.

19. A diagnostic kit comprising
   (a) the nucleic acid molecule according to claim 1; and/or
   (b) the polypeptide of claim 17.

20. A method for synchronizing and/or retarding cell growth in a cell culture population comprising
   (a) transforming a cell culture population with a vector comprising the nucleic acid molecule of claim 1 under the condition that said nucleic acid molecule is overexpressed, such that the cell growth is inhibited; and
   (b) the cell growth is resumed due to repression of the expression of said nucleic acid molecule.

21. A method for the preparation of a polypeptide according to claim 17 comprising preparing a vector comprising the nucleic acid molecule of claim 2 or a nucleic acid molecule comprising the sequence of SEQ ID No: 1 or SEQ ID No: 3.

22. An isolated polypeptide produced by the method of claim 16.

23. A composition comprising the vector of claim 6.

24. A method for screening for dominant negative mutants in *Saccharomyces cerevisiae* comprising the steps of culturing the organisms which are to be screened in or on media containing fluoro-orotic acid (FOA); detecting whether there is growth of said organisms; and verifying the mutation by performing plasmid rescue procedure.

25. A diagnostic kit comprising the vector of claim 6.

* * * * *

SEQUENCE LISTING

<160> NUMBER OF SEQ ID NOS: 6

<210> SEQ ID NO 1
<211> LENGTH: 465
<212> TYPE: DNA
<213> ORGANISM: Homo sapiens

<400> SEQUENCE: 1

```
atggcagatg acttggactt cgagacagga gatgcagggg cctcagccac cttcccaatg      60
cagtgctcag cattacgtaa gaatggcttt gtggtgctca aaggccggcc atgtaagatc     120
gtcgagatgt ctacttcgaa gactggcaag cacggccacg ccaaggtcca tctggttggt     180
attgacatct ttactgggaa gaaatatgaa gatatctgcc cgtcaactca taatatggat     240
gtccccaaca tcaaaaggaa tgacttccag ctgattggca tccaggatgg gtacctatca     300
ctgctccagg acagcgggga ggtacgagag gaccttcgtc tccctgaggg agaccttggc     360
aaggagattg agcagaagta cgactgtgga gaagagatcc tgatcacggt gctgtctgcc     420
atgacagagg aggcagctgt tgcaatcaag gccatggcaa aataa                     465
```

<210> SEQ ID NO 2
<211> LENGTH: 154

```
<212> TYPE: PRT
<213> ORGANISM: Homo sapiens

<400> SEQUENCE: 2

Met Ala Asp Asp Leu Asp Phe Glu Thr Gly Asp Ala Gly Ala Ser Ala
 1               5                  10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 3
<211> LENGTH: 474
<212> TYPE: DNA
<213> ORGANISM: Saccharomyces cerevisiae

<400> SEQUENCE: 3
atgtctgacg aagaacatac ctttgaaact gctgacgctg gttcctccgc cacctaccca      60
atgcaatgtt ctgccttgag aaagaacggt ttcgttgtca tcaagagtag accatgtaag     120
attgtcgaca tgtccacttc taagactggt aagcacggtc acgctaaagt ccatttggtt     180
gccattgata tcttcactgg taagaagttg aagatttgt  ctccatctac tcacaacatg     240
gaagttccag ttgtcaagag aaacgaatac caattgttgg acattgatga cggtttcttg     300
tctttgatga acatggacgg tgacactaag gatgatgtca aggctccaga aggtgaattg     360
ggtgacagtt tgcaaactgc ttttgatgaa ggtaaggact tgatggttac catcatctcc     420
gctatgggtg aagaagccgc catctccttc aaggaagctg ctagaaccga ttaa           474

<210> SEQ ID NO 4
<211> LENGTH: 157
<212> TYPE: PRT
<213> ORGANISM: Saccharomyces cerevisiae

<400> SEQUENCE: 4

Met Ser Asp Glu Glu His Thr Phe Glu Thr Ala Asp Ala Gly Ser Ser
 1               5                  10                  15

Ala Thr Tyr Pro Met Gln Cys Ser Ala Leu Arg Lys Asn Gly Phe Val
            20                  25                  30

Val Ile Lys Ser Arg Pro Cys Lys Ile Val Asp Met Ser Thr Ser Lys
        35                  40                  45

Thr Gly Lys His Gly His Ala Lys Val His Leu Val Ala Ile Asp Ile
    50                  55                  60
```

Phe Thr Gly Lys Lys Leu Glu Asp Leu Ser Pro Ser Thr His Asn Met
65                  70                  75                  80

Glu Val Pro Val Val Lys Arg Asn Glu Tyr Gln Leu Leu Asp Ile Asp
                85                  90                  95

Asp Gly Phe Leu Ser Leu Met Asn Met Asp Gly Asp Thr Lys Asp Asp
            100                 105                 110

Val Lys Ala Pro Glu Gly Glu Leu Gly Asp Ser Leu Gln Thr Ala Phe
        115                 120                 125

Asp Glu Gly Lys Asp Leu Met Val Thr Ile Ile Ser Ala Met Gly Glu
    130                 135                 140

Glu Ala Ala Ile Ser Phe Lys Glu Ala Ala Arg Thr Asp
145                 150                 155

<210> SEQ ID NO 5
<211> LENGTH: 510
<212> TYPE: DNA
<213> ORGANISM: Dictyostelium discoideum

<400> SEQUENCE: 5
atgaaaccat taataatgga gtacaacaaa atgtcagata cgaagctttt agatgtcgaa      60
gactacgccc aagccggttc aggtgcttca ttaaccttcc caattcaatg ttcagcatta     120
agaaagaacg gtttcgtcgt cattaaaggt ttcccatgta agattgttga tatgtcaact     180
tccaaaaccg gtaaacacgg tcacgccaaa gttaacatca ctgctatcga tatcttcact     240
ggtaagaaat acgaagaaat tgcccatca actcacaaca ttgatgtacc aaatgtcagc     300
agaaaggaat acaccgttat ggatgttcaa gatggttact tatcactctt ggatgctggt     360
ggtgaagtca agaagatct tgccctccca gaagatgata ttggtaaaga aattacccaa     420
atgttaaaag aaggtaaaga gccattagtt tcagtcatct ctgctttagg taaagaaggt     480
gtcgtctctg ttaaagtcag caacaattaa                                     510

<210> SEQ ID NO 6
<211> LENGTH: 169
<212> TYPE: PRT
<213> ORGANISM: Dictyostelium discoideum

<400> SEQUENCE: 6

Met Lys Pro Leu Ile Met Glu Tyr Asn Lys Met Ser Asp Asn Glu Ala
1               5                   10                  15

Leu Asp Val Glu Asp Tyr Ala Gln Ala Gly Ser Gly Ala Ser Leu Thr
            20                  25                  30

Phe Pro Ile Gln Cys Ser Ala Leu Arg Lys Asn Gly Phe Val Val Ile
        35                  40                  45

Lys Gly Phe Pro Cys Lys Ile Val Asp Met Ser Thr Ser Lys Thr Gly
    50                  55                  60

Lys His Gly His Ala Lys Val Asn Ile Thr Ala Ile Asp Ile Phe Thr
65                  70                  75                  80

Gly Lys Lys Tyr Glu Glu Ile Cys Pro Ser Thr His Asn Ile Asp Val
                85                  90                  95

Pro Asn Val Ser Arg Lys Glu Tyr Thr Val Met Asp Val Gln Asp Gly
            100                 105                 110

Tyr Leu Ser Leu Leu Asp Ala Gly Gly Glu Val Lys Glu Asp Leu Ala
        115                 120                 125

Leu Pro Glu Asp Asp Ile Gly Lys Glu Ile Thr Gln Met Leu Lys Glu
    130                 135                 140

-continued

```
Gly Lys Glu Pro Leu Val Ser Val Ile Ser Ala Leu Gly Lys Glu Gly
145                 150                 155                 160

Val Val Ser Val Lys Val Ser Asn Asn
                165
```